United States Patent [19]
Burnett

[11] 4,213,213
[45] Jul. 22, 1980

[54] SUPPORT DEVICE

[76] Inventor: John S. Burnett, "New Cottage", 51 Coldharbour La., Bushey, Herts., England, WD2 3NU

[21] Appl. No.: 932,956

[22] Filed: Aug. 11, 1978

[51] Int. Cl.² ............................................. A47C 3/00
[52] U.S. Cl. .......................................... 5/450; 5/454; 297/284
[58] Field of Search ..................... 5/91, 337, 339, 340; 297/284

[56] References Cited
U.S. PATENT DOCUMENTS

| 3,416,169 | 12/1968 | Emery ..................................... 5/441 |
| 3,608,961 | 9/1971 | VonHeek .................................. 5/450 |
| 3,840,920 | 10/1974 | Voelker ................................... 5/450 |
| 3,848,281 | 11/1974 | Mathews .................................. 5/436 |
| 4,055,866 | 11/1977 | Evans ...................................... 5/449 |

*Primary Examiner*—Casmir A. Nunberg
*Attorney, Agent, or Firm*—Lawrence E. Laubscher

[57] ABSTRACT

A support device, for the physically handicapped is disclosed comprising a cruciform airtight bag of synthetic plastics material filled with a granular material, for use as a liner for a conventional chair. The bag can be deflated to lock the granular material into a rigid structure which supports comfortably a physically handicapped person sitting in the chair.

6 Claims, 3 Drawing Figures

SUPPORT DEVICE

BACKGROUND OF THE INVENTION

This invention relates to a support device adapted to conform to the shape of and to support a body, the device of the invention having particular application to providing support for physically handicapped and deformed people.

SUMMARY OF THE INVENTION

In accordance with my invention there is provided a support device for conforming to the shape of and for supporting a body, comprising an airtight bag of a configuration which includes a plurality of outwardly extending arms. The bag contains a particulate material. A valve means is provided to permit the bag to be maintained in a deflated condition. The bag and the material therein are selected to be adequately flexible, when the bag is deflated (i.e., partially inflated), to assume a shape conforming to that of the body of a physically handicapped person to be supported, and such that there is formed for the body a rigid support in the conformed shape upon deflation of the bag.

In use of the device of the invention, the body to be supported presses into contact with the undeflated bag such that the particulate material flows in the bag and conforms closely to the shape of the body. The bag is then deflated and the particulate material is thereby compressed into a rigid structure that has a shape conforming to that of the body, thereby providing support for the body.

In accordance with my invention, the outwardly extending arm configuration of the bag has the special advantage that it can be used as a liner for a conventional chair, allowing a physically handicapped person to sit comfortably in the chair while being properly supported. Preferably, the arms of the bag define a generally cruciform arrangement.

BRIEF DESCRIPTION OF THE FIGURES

In order that the invention may be more fully understood and readily carried into effect, an embodiment thereof will now be described by way of example with reference to the accompanying drawings in which.

DETAILED DESCRIPTION

Figure 1:
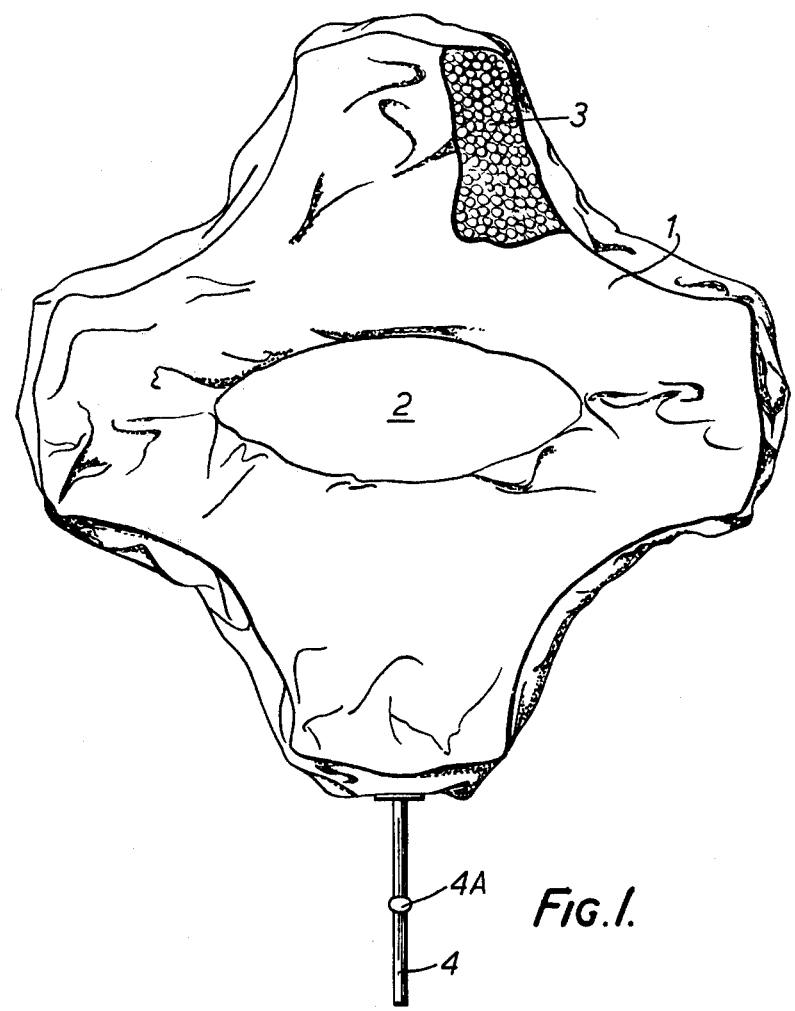
FIG. 1 is a plan view of a support device in accordance with the invention.
Figure 2:
FIG. 2 is an end view of the device of FIG. 1.
Figure 3:
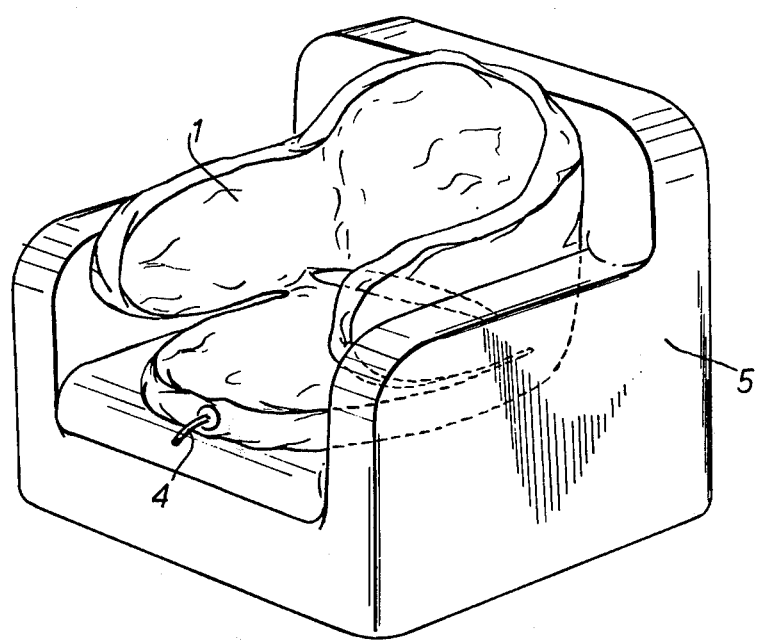
FIG. 3 illustrates the device of FIG. 1 installed in an armchair.

The device comprises a generally flat, flexible bag 1 of synthetic plastics material, which is generally cruciform in shape and has a central circular aperture 2 therein. The bag 1 is airtight and is filled with granular material consisting of granules 3 of polyether foam and of expanded polystyrene, and includes a valve 4A in a tube 4 to permit deflation of the bag. As shown in FIG. 3, the device is used as a liner for a conventional chair 5, the arms of the cruciform shaped bag being used as a base, sides and a back liner respectively for the chair.

When the bag is undeflated it is relatively limp and is like a conventional cushion, the granules 3 being able to flow relative to one another in the bag 1. However, upon the bag being evacuated of air, the air pressure outside the bag 1 acts on the granules 3 so as to compress them together such that the bag forms a rigid structure.

In use of the device, it is placed in an undeflated condition in a conventional chair as shown in FIG. 3, and a physically handicapped or deformed person then sits upon the bag. Since the bag is undeflated, the granules flow relative to one another such that the bag conforms closely to the shape of the person sitting in the chair. The bag is then deflated by the sedentary person sucking the tube 4, the valve 4A maintaining the bag in a deflated condition. Accordingly, a rigid bag structure is formed which conforms closely to the shape of the sedentary person providing them with a comfortable firm support. The generally cruciform shape of the bag has the advantage of allowing the device to fit neatly into a conventional chair to allow support to be provided at the back and sides of the sitter.

I claim:

1. A device for supporting a human body in a chair, comrpising
   (a) a hollow airtight bag member having a generally cruciform configuration;
   (b) a particulate material arranged within said bag member; and
   (c) means for controlling the degree of inflation of said bag member between a flexible partially inflated condition and a rigid deflated condition, whereby when said bag is partially inflated, said particulate material is distributed within said bag member to conform with the configuration of the body being supported, and when said bag member is deflated, said bag member and said particulate material rigidly support the body in a chair.

2. A support device as defined in claim 1, wherein said particulate material comprises a plurality of granules of expanded polystyrene and polyether foam.

3. A support device as defined in claim 2, wherein said bag member is formed from a synthetic plastics material.

4. A support device as defined in claim 3, wherein said bag member includes a centrally arranged aperture.

5. A method of supporting a human body in a chair with a hollow support device having a generally cruciform configuration and containing a particulate material, comprising the steps of
   (a) partially inflating the support device;
   (b) conforming the support device and particulate material with the configuration of the body being supported; and
   (c) deflating the support device to provide a rigid support for the body.

6. A method as defined in claim 5, and further comprising the step of placing the support device in a chair with the limbs of the device overlying the chair seat sides and back, respectively.

* * * * *